US010899722B2

(12) United States Patent
Schnatterer et al.

(10) Patent No.: US 10,899,722 B2
(45) Date of Patent: Jan. 26, 2021

(54) PROCESS FOR THE PREPARATION OF FLUOROALKYLNITRILES AND THE CORRESPONDING FLUOROALKYLTETRAZOLES

(71) Applicant: Bayer CropScience Aktiengesellschaft, Monheim am Rhein (DE)

(72) Inventors: Albert Schnatterer, Leverkusen (DE); Jan Vermehren, Idstein (DE); Edith Beckmann, Cologne (DE); Claus-Christian Haeselhoff, Gladbeck (DE); Tim Hammerer, Baesweiler (DE); Stefan Grasser, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 19 days.

(21) Appl. No.: 16/488,289

(22) PCT Filed: Feb. 22, 2018

(86) PCT No.: PCT/EP2018/054385
§ 371 (c)(1),
(2) Date: Aug. 23, 2019

(87) PCT Pub. No.: WO2018/158131
PCT Pub. Date: Sep. 7, 2018

(65) Prior Publication Data
US 2019/0375721 A1 Dec. 12, 2019

(30) Foreign Application Priority Data
Feb. 28, 2017 (EP) .................... 17158376

(51) Int. Cl.
| | | |
|---|---|---|
| C07D 257/04 | (2006.01) | |
| C07C 253/20 | (2006.01) | |
| B01J 29/40 | (2006.01) | |
| B01J 29/70 | (2006.01) | |
| C07C 253/34 | (2006.01) | |

(52) U.S. Cl.
CPC ............ *C07D 257/04* (2013.01); *B01J 29/40* (2013.01); *B01J 29/7038* (2013.01); *C07C 253/20* (2013.01); *C07C 253/34* (2013.01)

(58) Field of Classification Search
CPC .......................... C07D 257/04; C07C 253/20
See application file for complete search history.

(56) References Cited

U.S. PATENT DOCUMENTS

| | | | |
|---|---|---|---|
| 3,274,229 A | 9/1966 | Verbanic | |
| 8,203,015 B2* | 6/2012 | Lui | ........................ C07C 253/20 558/313 |

FOREIGN PATENT DOCUMENTS

| | | |
|---|---|---|
| CN | 102746190 A | 10/2012 |
| CN | 103804231 A | 5/2014 |
| DE | 3600811 A1 | 8/1987 |
| EP | 729940 A2 | 9/1996 |

OTHER PUBLICATIONS

PCT International Search Report for PCT/EP2018/054385, dated May 15, 2018.
Crawford, et al, "Synthesis and characterization of perfluorinated nitriles and the corresponding sodium 5-perfluoroalkyltetrazolate salts," Journal of Fluorine Chemistry, (2008), vol. 129: 1199-1205.
Naik, et al., "Synthesis of acetonitrile by dehydration of acetamide on an active ZnO catalyst: A comparison with zeolite catalysts", Indian Journal of Chemical Technology, (1998), vol. 5: 405-406.
Rao, et al., "Synthesis of nitriles from carboxamides with zeolites," Chemistry and Industry, (1984), p. 270.
Subrahmanyam, et al., "Preparation of Acetonitrile by Acetamide Dehydration over Zeolites," J. Indian Chem., (1992), vol. 69: 681-682.
Gilman, et al., "2,2,2-Trifluoroethylamine and 2,2,2-Trifluorodiazoethane," J. Organic Chem., (1943), vol. 65: 1458-1460.

* cited by examiner

*Primary Examiner* — Golam M Shameem
(74) *Attorney, Agent, or Firm* — McBee Moore & Vanik IP, LLC

(57) ABSTRACT

The present invention relates to a process for the preparation of fluoroalkylnitriles and the corresponding fluoroalkyltetrazoles starting from fluorinated carboxamides.

10 Claims, 1 Drawing Sheet

Diagrammatic representation of the preparation process according to the invention
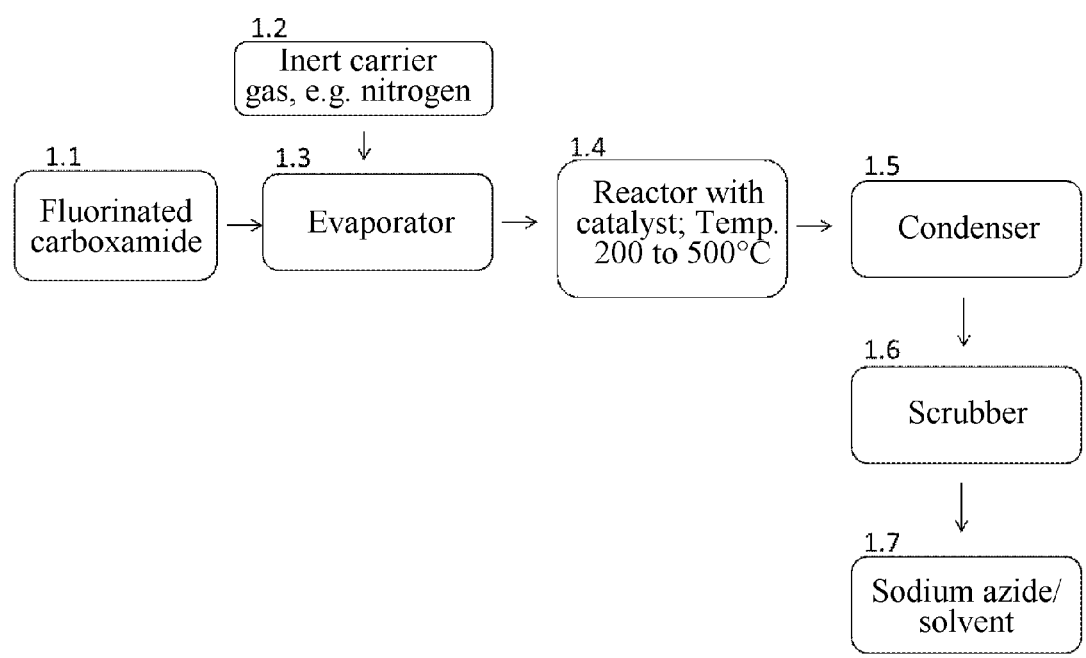

PROCESS FOR THE PREPARATION OF FLUOROALKYLNITRILES AND THE CORRESPONDING FLUOROALKYLTETRAZOLES

CROSS-REFERENCE TO RELATED APPLICATIONS

This application is the National Stage entry of International Application No. PCT/EP2018/054385, filed 22 Feb. 2018, which claims priority to European Patent Application No. 17158376.8, filed 28 Feb. 2017.

BACKGROUND

Field

The present invention relates to a process for the preparation of fluoroalkylnitriles and the corresponding fluoroalkyltetrazoles starting from fluorinated carboxamides.

Description of Related Art

Fluoroalkylnitriles and the corresponding fluoroalkyltetrazoles are important intermediates for the preparation of agrochemical active substances.

EP 729 940 A2 reports the synthesis of fluorinated nitriles by reaction of trifluoroacetic anhydride in a polar amide solvent, such as, e.g., DMF.

CN 103804231A (2014) discloses the preparation of trifluoroacetonitrile from the amide by addition of trifluoroacetic anhydride in carbon tetrachloride.

U.S. Pat. No. 3,274,229 A describes the dehydration of perfluorinated amides to give the corresponding nitriles using Lewis acids, such as, e.g., $ZnCl_2$.

CN 102746190A (2012) describes the preparation of trifluoroacetonitrile from the amide by the polyphosphoric acid/phosphoric acid catalyst system.

Jones et al. (Journal of Organic Chemistry (1943, 65, 1458)) describes the dehydration of trifluoroacetamide by means of phosphorus pentoxide.

Kumar et al. (Chemistry and Industry, 1984, vol. 7, 270, 1984) describes the dehydration of simply structured, thermally very stable, carboxamides, such as benzamide, phenylacetamide, nicotinamide and isopentanamide, in the form of their vapours on ZSM-5 zeolites at 400° C. with yields of 85-90%. The publication does not describe the dehydration of fluoroalkylacetamides with zeolites.

Prasad et al. (Journal of the Indian Chemical Society, 1992, 69(10), 681-682) discloses the preparation of acetonitrile through acetamide dehydration over zeolites. In this publication also, no fluoroalkylacetamides are used as starting materials.

Fernandez et al. (Indian Journal of Chemical Technology, 1998, vol. 5(6), 405-406) reports the synthesis of acetonitrile through dehydration on active ZnO catalysts in comparison with zeolite catalysts. The publication does not describe the use of fluoroalkylacetamides as starting materials.

DE3600811A1 discloses the preparation of nitriles through catalytic dehydration of carboxamides on zeolitic catalysts in the presence of ammonia. The publication does not describe the use of fluoroalkylacetamides as starting materials.

In some of the processes described in the state of the art, dehydrating reagents (such as, e.g., trifluoroacetic anhydride) have to be used in multifold excess. It is necessary to recycle the materials and solvents used. When phosphorus pentoxide is used, reactions of this type generally result in solidified mixtures which can no longer be stirred, which are an obstacle to an implementation on a large-scale.

None of the processes described in the state of the art describes the dehydration of fluorinated carboxamides with catalysts such as, for example, zeolites or aluminium phosphates. The use of such catalysts has the advantage that these are environmentally friendly and inexpensive and can be reused for the further preparation of fluoroalkylnitriles (e.g. in a continuous process). Hitherto, a person skilled in the art started from the assumption that the dehydration of fluorinated carboxamides with such catalysts does not lead to the desired results due to the reactivity of the fluorine residues. This is disproved by the present invention.

SUMMARY

Proceeding from the state of the art, the object of the present invention is to provide the most efficient, selective and inexpensive process possible for the preparation of fluorinated alkylnitriles and the fluorinated alkyltetrazoles obtainable therefrom, which can preferably be carried out in a simple manner. The fluorinated alkylnitriles or fluorinated alkyltetrazoles obtainable with this process which is striven for should preferably in this connection be obtained with high selectivity and in high yield. In particular, the process striven for should enable the desired target compounds to be obtained without the need for complex purification methods.

The object was achieved according to the present invention by a process for the preparation of fluoroalkylnitriles of the general formula (I) by catalytic gas-phase dehydration,

in which
$X^1$ and $X^2$ are, independently of each other, a halogen, hydrogen or methyl,
characterized in that
fluorinated carboxamides of the formula (II)

in which $X^1$ and $X^2$ have the abovementioned meanings, are converted into the gas phase and are reacted in the presence of catalysts chosen from the group of zeolites, aluminium phosphate, zirconium dioxide and heteropolyacids (preferably chosen from the group of zeolites and aluminium phosphate and more preferably still chosen from the group of the zeolites).

DETAILED DESCRIPTION OF A PREFERRED EMBODIMENT

In this connection, $X^1$ and $X^2$ are, independently of each other, preferably fluorine, chlorine, hydrogen or methyl and more preferably still only fluorine.

In an additional preferred embodiment of the invention, the fluoroalkylnitriles of the general formula (I),

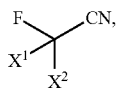
(I)

after preparation according to the process described above, are reacted directly with sodium azide in the presence of a solvent to give the corresponding fluoroalkyltetrazoles of the general formula (III)

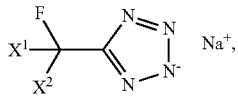
(III)

in which $X^1$ and $X^2$ have the abovementioned meanings.

The fluoroalkyltetrazole of the formula (III) is in this connection preferably present in the form of the sodium salt.

The fluorinated alkylamides of the formula (II) used according to the present invention are commercially available or can be easily prepared by processes known in the literature (WO 03/080563).

The preparation of the fluoroalkyltetrazoles from the fluoroalkylnitriles has, for example, also been described in the Journal of Fluorine Chemistry, 120 (2008), 1199-1205.

Surprisingly, the fluorinated alkylnitriles of the formula (I) or fluoroalkyltetrazoles of the general formula (III) correspondingly prepared therefrom can be reliably prepared under the conditions according to the invention in high purity with good selectivities and yields. In this connection, the process according to the invention does not exhibit the disadvantages described in connection with the state of the art.

In the context of the present invention, the term halogens or halides includes, unless otherwise defined, those elements which are chosen from the group consisting of fluorine, chlorine, bromine and iodine, preference being given to the use of fluorine, chlorine and bromine and particular preference being given to the use of fluorine and chlorine.

Optionally substituted groups can be mono- or polysubstituted, it being possible for the substituents in the case of poly substitutions to be identical or different.

Gas-Phase Dehydration (Steps 1.1 to 1.5 in FIG. 1)

First, a reactor is filled with a catalyst described according to the invention (1.4 in FIG. 1) and optionally rendered inert with nitrogen. The desired reactor temperature (preferably between 200-500° C. and more preferably still between 250-350° C.) is then set. Subsequently, fluorinated carboxamide of the formula (II) (preferably in combination with an inert carrier gas, such as nitrogen) is changed to the reaction gas (1.2 in FIG. 1). The fluorinated carboxamide of the formula (II) existing in solid form at ambient temperature is preferably (in a heated piston pump) melted (1.1 in FIG. 1) and fed via a heated pipe to an upstream evaporator (1.3 in FIG. 1), in which it is converted into the gaseous state. The temperature in the evaporator is in this connection preferably between 200 and 300° C. If the fluorinated carboxamide of the formula (II) is already in the liquid state, it is fed directly to the evaporator via a pump. As a rule, there is no limitation for the amount of amide. A space velocity of the catalyst which causes neither an excessively high pressure drop nor an excessively fast catalyst deactivation nor an incomplete reaction is viable industrially. Byproducts or unreacted starting materials are condensed out using a condenser (1.5 in FIG. 1) at temperatures of preferably between 1° C. and 10° C.

Catalysts

Zeolites are crystalline aluminosilicates which occur naturally in numerous polymorphs but can also be produced synthetically, and inter alia can be used as catalysts.

Zeolites can be described by the following empirical formula:

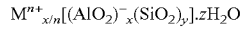

Here, M is typically a cation of an alkali metal or alkaline earth metal or ammonium ion which is necessary for the electrical charge equalization of the negatively charged aluminium/oxygen tetrahedra. "n" is the charge of the cation, which is typically 1 or 2. The molar ratio of $SiO_2$ to $AlO_2$ or y/x in the empirical formula is referred to as the modulus. The letter z indicates the number of the water molecules taken up by the crystal.

It was substantiated, by several experiments, that an active zeolite catalyst particularly suitable for the preparation of fluoroalkylnitriles should be present in the proton form, i.e. M=H and n=1 Depending on the zeolite, water is released from the crystal at approximately 250° C., so that z depends on the precise reaction conditions. The y/x molar ratio has an influence on the number of the Lewis acid Al centres and on the relative strength of them among themselves. It is variable within wide ranges. Molar ratios of 10 to 120 are preferred and molar ratios of 20 to 100 are particularly preferred.

Zeolites in the proton form (H form) can also be prepared at the beginning of the process (virtually in situ) inside the reactor. All cations which at relatively high temperatures (>150° C.) decompose in such a way that a volatile component and a proton are formed are suitable for this. Ammonium cations of the general form $NHR_3^+$, which decompose into protons and $NR_3$, are also accordingly preferred. The ammonium cation (R=H), i.e. $NH_4^+$, is particularly preferred.

However, it is also possible to choose larger organic ammonium cations of the form $NR_3R'^+$, in which the organic radical R' decomposes by Hofmann elimination in such a way that an olefin and protons are formed from the radical R'. Thus, it is, e.g., known that a butyl radical can be cleaved by Hofmann elimination into a proton and into a butene (preferably 1-butene). The $NR_3$ formed from this should be as volatile as possible.

Particularly preferably according to the invention, the zeolites which can be used exhibit a structure which is chosen from the pentasil and MWW structure types and very particularly preferably from the MFI, MEL, mixed structures of MFI and MEL and MWW structure types. Use is more preferably still made of zeolites of the ZSM-5 or MCM-22 type. The descriptions of the structure types of the zeolites correspond to the specifications in W. M. Meier, D. H. Olson and Ch. Baerlocher, "Atlas of Zeolite Structure Types", Elsevier, 3rd edition, Amsterdam, 2001. The synthesis of the zeolites is known to a person skilled in the art and can, for example, be carried out starting from alkali metal aluminate, alkali metal silicate and amorphous $SiO_2$ under hydrothermal conditions. In this connection, the type of the channel systems formed in the zeolite can be controlled via organic template molecules, via the temperature and additional experimental parameters.

The space velocity of the catalyst is given at constant catalyst weight (limited by the maximum possible pressure drop for the installation). In this connection, a characteristic number in reaction engineering is concerned which gives the mass flow rate or mole flow rate of starting material with regard to the catalyst weight. Frequently, the volume of the catalyst bed is also used as reference quantity (cf. Gas Hourly Space Velocity or Weight Hourly Space Velocity). As a rule, the starting material is applied to the bed diluted with an inert gas. However, this diluting is not stated. In the present invention, it has been shown that, with an amount of starting material of ~50 mmol at a metering time between 8 and 80 minutes and a catalyst weight between 2 g and 5 g, there is a space velocity of the catalyst of 2 to 1000 mmol of amide/(g*h), preferably of 3 to 700 mmol of amide/(g*h) and particularly preferably of 4 to 500 mmol of amide/(g*h).

The pressure drop is influenced by the shape of the catalyst particle. Zeolites can be used as powder. However, the pressure drop is then often exceptionally high. In order to reduce the pressure drop of a zeolite powder bed, this powder bed can be constructed, through inert material, e.g. from glass, as a somewhat more loosely packed formed piece. For use as catalyst, the zeolites are accordingly frequently also used as formed bodies, in order to keep the pressure drop of the bed low. The catalyst is mixed with a binder for the forming. The normal binders known to a person skilled in the art, such as binders containing aluminium oxide and/or Si, are suitable as binders. Si-containing binders are particularly preferred in this connection; tetraalkoxysilanes, polysiloxanes and colloidal $SiO_2$ sols are suitable in particular. The use of formed zeolites is particularly preferred. All conceivable geometric shapes which lead to a loose packing of the bed are possible. Balls, cylinders and stars in particular are preferred.

In many cases, it can be advantageous to dilute the zeolite formed pieces even with other inert formed pieces in order to reduce possible hotspots occurring as a result of an exothermic reaction and to reduce the catalyst deactivation possibly accompanying this.

Zeolites are frequently used catalysts especially in the petroleum industry. They are used for the isomerization or for the cracking of hydrocarbons. In addition, zeolites can function in different catalysis fields as "carriers", to which the actually catalytically active components (as a rule, metals) are then applied. In addition, zeolites are also used for purification/drying (molecular sieves). Accordingly, the zeolites are readily available commercially. Clariant, BASF, Zeocem®, Grace, Zeolyst, Zeo Inc. and the like, for example, function as suppliers. ExxonMobile also uses many zeolites.

An additional possibility for suitable catalysts is a system of materials in which, in addition to aluminium, silicon and oxygen (cf. aluminosilicates; zeolites), phosphorus is even involved. Phosphorus can be mixed with the zeolite in order to increase the Brönstedt acidity. The phosphorus can be supplied to the zeolite by any conventional means, such as mixing the zeolite with an aqueous solution of a phosphorus compound, such as a phosphate salt or phosphoric acid. Ammonium hydrogenphosphates are preferred phosphorus sources.

In an additional embodiment of the invention, aluminium phosphates or phosphorus-doped aluminium oxides are used as catalysts. Such materials can either themselves be prepared or are commercially available. Clariant is a possible supplier of aluminium phosphates.

Aluminium phosphate can be obtained by reaction of aluminium nitrate and ammonium phosphate in aqueous solution, in which in particular an aqueous solution of aluminium nitrate and an aqueous solution of ammonium phosphate, which are prepared in a phosphorus/aluminium molar ratio of 0.5 to 1.5, are mixed and this solution is then preferably adjusted to a pH of 7 to 9 by addition of concentrated ammonium hydroxide solution. After the hydrogel obtained has been dried, this is heated (calcined) to a temperature of over 500° C. The phosphorus-doped aluminium oxide is prepared by mixing aluminium oxide and phosphoric acid solution (impregnation). This solution typically comprises from 0.1% to 30% by weight of phosphoric acid in the weight ratio of phosphoric acid to aluminium oxide. The aluminium oxide has a specific surface of greater than 1 $m^2/g$, preferably more than 10 $m^2/g$. After removing the water, the product is heated at a temperature of over 500° C. in order to fix the phosphorus to the aluminium oxide.

In an additional embodiment of the invention, zirconium dioxide is used as catalyst or catalyst constituent. Zirconium dioxide is known as ceramic material. Zirconium dioxide has the ability, at relatively high temperature, to electrolytically conduct oxygen ions. This property is made use of in order to measure different oxygen partial pressures, e.g. between exhaust gases and air (lambda probe in cars). Zirconium dioxide occurs in different polymorphs which can be converted into one another at higher temperatures: monoclinic (up to 1173° C.)→tetragonal (2370° C.)→cubic (2690° C.). In order to also have the zirconium dioxide available for high temperature applications, without the mechanical stability of the zirconium dioxide being changed by change in volume with phase conversions, the ceramics industry for its part has carried out intensive work on stabilizing the phases through addition of other oxides. Zirconium dioxides stabilized with other elements (e.g., Hf, Y, W) are accordingly commercially available. In addition, it is known that zirconium dioxide can be converted into sulfated zirconium dioxide (cf. U.S. Pat. No. 5,149,862), which is characterized by a higher acidity. Zirconium dioxide is obtainable, e.g., from Saint-Gobain Norpro or Ceramtec.

Furthermore, heteropolyacids (e.g., phosphotungstic acid) are also conceivable as catalysts.

Reaction to Give the Fluoroalkyltetrazoles of the General Formula (III) (Steps 1.6 and 1.7 in FIG. 1)

In the process represented above, compounds of the general formula (I) are present in a hot gas stream. As a rule, inert compounds, such as, e.g., nitrogen, are added to the gas stream. The separation of the compounds of the general formula (I) is carried out by cooling in a cold trap. This can comprise, for assistance, a liquid or solid medium (solvent, activated carbon, or the like), in which compounds of the general formula (I) can be absorbed or adsorbed.

The desired compounds of the general formula (I) can be isolated from solvents, for example, by distillation.

However, it is not necessary to isolate compounds of the general formula (I). It is even advantageous to immediately (virtually in situ) react these compounds further, in particular if the nitrile obtained is very poisonous or highly reactive. It is known that nitriles can react with many reagents. The reactivity typically depends on the R radical in R—C≡N. Nitriles react with caustic ($OH^-$) reagents to give the corresponding carboxylic acids; "Pinner salts" can, with alcohols and HCl, be obtained from the nitrile and can, in subsequent steps, form carboxylic acid esters, orthoesters or protonated amidines.

It is also possible to hydrogenate compounds of the general formula (I) to give primary amines.

An additional possibility for the functionalization of nitriles is the reaction with 1,3-dipolar compounds, such as nitrile oxide, azide or diazoalkane. Such a reaction frequently results in heterocycles, which play a role in the preparation of biologically active compounds. Thus, a nitrile reacts with an azide to give a "tetrazolate", i.e. compounds of the general formula (III).

The in situ production of a nitrile according to formula (I) and the immediate reaction (without isolation) with an azide salt (preferably sodium azide) in a solvent to give the tetrazole compounds of the general formula (III) is particularly preferred according to the invention.

In this connection, the product-containing gas stream from the gas-phase dehydration described above is introduced via a scrubber (Step 1.6 in FIG. 1) into a mixture (preferably into a stirred suspension) of sodium azide in a solvent (1.7 in FIG. 1). Use is preferably made, for this reaction, of a polar aprotic solvent, such as, e.g., ketones, such as acetone, lactones, such as γ-butyrolactone, lactams, such as N-methyl-2-pyrrolidone, nitriles, such as acetonitrile, nitro compounds, such as nitromethane, tertiary carboxamides, such as dimethylformamide, urea derivatives, such as tetramethylurea or dimethylpropyleneurea (DMPU), sulfoxides, such as dimethyl sulfoxide (DMSO), sulfones, such as sulfolane, or carbonic esters, such as dimethyl carbonate or ethylene carbonate. Use is particularly preferably made of acetone or acetonitrile as solvent.

The scrubber (1.6 in FIG. 1) preferably contains a base for the separation of traces of acid, in order to prevent the formation of explosive nitrogen/hydrogen/acid (possibly arising by reaction of sodium azide with proton sources, such as inorganic acids, carboxylic acids, alcohols or water). This is not only extremely reactive but also reduces the amount of azide salt necessary for the intended reaction. As example, only slightly nucleophilic bases, such as pyridine or substituted pyridines and substituted or unsubstituted quinolines, can be used. Preferred examples of suitable bases are pyridine, picolines, quinoline, quinaldine and halogenated pyridines and particularly preferably 3-picoline.

In order to further increase the processing safety, sodium hydroxide solution (20%) can be connected downstream of the sodium azide reactor in, for example, two wash bottles (1.7 in FIG. 1). The reactor gas is subsequently so strongly diluted that it can, without danger, be fed to the used air.

The process described above is preferably carried out continuously. The flow velocities are preferably chosen so that the respective residence time in the reactor is in the range from 1.0 second to 1 minute, preferably from 1.0 second to 10 seconds. The pressure in the reactor is typically below 1 bar, preferably between 100 and 500 mbar and more preferably still below 300 mbar.

The desired compounds of the general formula (III) can be isolated, for example, by filtration. However, for this, the azide salt, as a general rule present in excess and not always very readily soluble in the solvent, should have been separated beforehand. Alternatively, extraction can be carried out with a somewhat less polar aprotic solvent.

It is conceivable to further react compounds of the general formula (III) for its part in situ, i.e. without isolation. This is in particular advantageous if the danger of an unintentional (explosive) decomposition of the tetrazolate with release of nitrogen is further minimized because of this.

The amount of sodium azide should be sufficiently large such that the nitrile can be completely converted in an industrially viable time. If the excess of azide is too large, the salt, which can potentially decompose with release of nitrogen, has to be again separated The azide/nitrile molar ratio is preferably between 1 and 10, more preferably between 1 and 5 and particularly preferably between 1 and 2.

The amount of polar aprotic solvent in which the azide salt is dissolved or suspended is not critical. Typical mixtures can comprise up to 20% by weight of azide.

The present invention is elucidated in detail by the examples which follow, although the examples should not be interpreted in such a manner that they restrict the invention.

PREPARATION EXAMPLES

FIG. 2: Representation of the preparation of sodium trifluoromethyltetrazolate starting from trifluoroacetamide

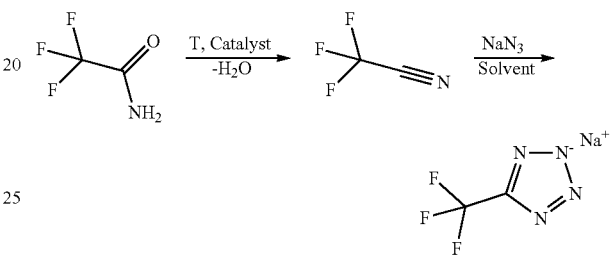

NaTFMT

Example 1

The reactor is filled with 5.0 g of HCZP 55E zeolite (Clariant) and rendered inert with nitrogen. After reaching the reaction temperature of 500° C., a nitrogen flow of 55 ml/min is set. The molten trifluoroacetamide is led at 0.5 ml/min into the upstream evaporator (T=250° C.) and from there likewise into the reactor. The mean residence time in the reaction zone results from the reactor architecture and is 5.4 seconds. The product gas stream is first led through a high-efficiency condenser cooled to +4° C. and subsequently introduced, via a scrubber filled with 3-picoline, into a suspension of 10% by weight of sodium azide in acetone. The resulting solution of sodium trifluoromethyltetrazolate (NaTFMT) in acetone is analysed via $^{19}$F NMR using an internal standard. The yield of NaTFMT, based on the amount of trifluoroacetamide used, is 1%.

Example 2

The reactor is filled with 5.0 g of HCZP 90E zeolite (Clariant) and rendered inert with nitrogen. After reaching the reaction temperature of 350° C., a nitrogen flow of 55 ml/min is set. The molten trifluoroacetamide is led at 0.5 ml/min into the upstream evaporator (T=250° C.) and from there likewise into the reactor. The mean residence time in the reaction zone results from the reactor architecture and is 5.4 seconds. The product gas stream is first led through a high-efficiency condenser cooled to +4° C. and subsequently introduced, via a scrubber filled with 3-picoline, into a suspension of 10% by weight of sodium azide in acetone. The resulting solution of sodium trifluoromethyltetrazolate (NaTFMT) in acetone is analysed via $^{19}$F NMR using an internal standard. The yield of NaTFMT, based on the amount of trifluoroacetamide used, is 3%.

Example 3

The reactor is filled with 2.0 g of HCZP 27E zeolite (Clariant) and rendered inert with nitrogen. After reaching the reaction temperature of 350° C., a nitrogen flow of 99 ml/min is set. The molten trifluoroacetamide is led at 0.05 ml/min into the upstream evaporator (T=250° C.) and from there likewise into the reactor. The mean residence time in the reaction zone results from the reactor architecture and is 2.9 seconds. The product gas stream is first led through a high-efficiency condenser cooled to +4° C. and subsequently introduced, via a scrubber filled with 3-picoline, into a suspension of 10% by weight of sodium azide in acetone. The resulting amount of sodium trifluoromethyltetrazolate (NaTFMT) in acetone is analysed via $^{19}$F NMR using an internal standard. The yield of NaTFMT, based on the amount of trifluoroacetamide used, is 18%.

Example 4

The reactor is filled with 5.0 g of HCZP 55E zeolite (Clariant) and rendered inert with nitrogen. After reaching the reaction temperature of 400° C., a nitrogen flow of 99 ml/min is set. The molten trifluoroacetamide is led at 0.5 ml/min into the upstream evaporator (T=250° C.) and from there likewise into the reactor. The mean residence time in the reaction zone results from the reactor architecture and is 2.9 seconds. The product gas stream is first led through a high-efficiency condenser cooled to +4° C. and subsequently introduced, via a scrubber filled with 3-picoline, into a suspension of 10% by weight of sodium azide in acetone. The resulting amount of sodium trifluoromethyltetrazolate (NaTFMT) in acetone is analysed via $^{19}$F NMR using an internal standard. The yield of NaTFMT, based on the amount of trifluoroacetamide used, is 13%.

Example 5

The reactor is filled with 5.0 g of doped zirconium oxide SZ69157 (Saint-Gobain) and rendered inert with nitrogen. After reaching the reaction temperature of 400° C., a nitrogen flow of 99 ml/min is set. The molten trifluoroacetamide is led at 0.14 ml/min into the upstream evaporator (T=250° C.) and from there likewise into the reactor. The mean residence time in the reaction zone results from the reactor architecture and is 2.9 seconds. The product gas stream is first led through a high-efficiency condenser cooled to +4° C. and subsequently introduced, via a scrubber filled with 3-picoline, into a suspension of 10% by weight of sodium azide in acetone. The resulting amount of sodium trifluoromethyltetrazolate (NaTFMT) in acetone is analysed via $^{19}$F NMR using an internal standard. The yield of NaTFMT, based on the amount of trifluoroacetamide used, is 18%.

Example 6

The reactor is filled with 1.2 g of doped aluminium phosphate HCZA (Clariant) as powder diluted with 9 g of inert material (glass beads) and rendered inert with nitrogen. After reaching the reaction temperature of 400° C., a nitrogen flow of 99 ml/min is set. The molten trifluoroacetamide is led at 0.14 ml/min into the upstream evaporator (T=250° C.) and from there likewise into the reactor. The mean residence time in the reaction zone results from the reactor architecture and is 2.9 seconds. The product gas stream is first led through a high-efficiency condenser cooled to +4° C. and subsequently introduced, via a scrubber filled with 3-picoline, into a suspension of 10% by weight of sodium azide in acetone. The resulting amount of sodium trifluoromethyltetrazolate (NaTFMT) in acetone is analysed via $^{19}$F NMR using an internal standard. The yield of NaTFMT, based on the amount of trifluoroacetamide used, is 4%.

Example 7

The reactor is filled with 2.0 g of HCZP 55E zeolite (Clariant) and rendered inert with nitrogen. After reaching the reaction temperature of 300° C., a nitrogen flow of 150 ml/min is set. The molten trifluoroacetamide is led at 0.05 ml/min into the upstream evaporator (T=250° C.) and from there likewise into the reactor. The mean residence time in the reaction zone results from the reactor architecture and is 1.9 seconds. The product gas stream is first led through a high-efficiency condenser cooled to +4° C. and subsequently introduced, via a scrubber filled with 3-picoline, into a suspension of 10% by weight of sodium azide in acetone. The resulting amount of sodium trifluoromethyltetrazolate (NaTFMT) in acetone is analysed via $^{19}$F NMR using an internal standard. The yield of NaTFMT, based on the amount of trifluoroacetamide used, is 11%.

Example 8

The reactor is filled with 5.0 g of HCZP 55E zeolite (Clariant) and rendered inert with nitrogen. After reaching the reaction temperature of 350° C., a nitrogen flow of 150 ml/min is set. The molten trifluoroacetamide is led at 0.05 ml/min into the upstream evaporator (T=250° C.) and from there likewise into the reactor. The mean residence time in the reaction zone results from the reactor architecture and is 1.9 seconds. The product gas stream is first led through a high-efficiency condenser cooled to +4° C. and subsequently introduced, via a scrubber filled with 3-picoline, into a suspension of 10% by weight of sodium azide in acetone. The resulting amount of sodium trifluoromethyltetrazolate (NaTFMT) in acetone is analysed via $^{19}$F NMR using an internal standard. The yield of NaTFMT, based on the amount of trifluoroacetamide used, is 27%.

The invention claimed is:
1. A process for the preparation of a fluoroalkylnitrile of formula (I) by catalytic gas-phase dehydration,

in which
X$^1$ and X$^2$ are, independently of each other, a halogen, hydrogen or methyl,
comprising converting
a fluorinated carboxamide of formula (II)

in which $X^1$ and $X^2$ have the abovementioned meanings, into gas phase and reacting in the presence of a catalyst selected from the group of zeolites, aluminium phosphate, zirconium dioxide and heteropolyacids.

2. The process according to claim 1, wherein $X^1$ and $X^2$ are each time, independently of each other, fluorine, chlorine, hydrogen or methyl and optionally fluorine.

3. The process according to claim 1, wherein the catalyst is a zeolite.

4. The process according to claim 3, wherein the zeolite catalyst is present in proton form and the molar ratio of $SiO_2$ to $AlO_2$ is 10-120.

5. The process according to claim 3, wherein the zeolite exhibits a structure which is chosen from the group of pentasil and MWW.

6. The process according to claim 1, wherein a fluorinated carboxamide of formula (II) is converted at a temperature of 200-500° C. in the presence of the catalyst, optionally in a reactor, to give the fluoroalkylnitrile of formula (I).

7. The process according to claim 6, wherein the reaction takes place at a pressure of less than 1 bar.

8. The process according to claim 6, wherein the process is carried out continuously and the flow velocities are chosen so that respective residence time in the reactor is in a range from 1.0 second to 1 minute.

9. The process according to claim 1, wherein the fluoroalkylnitrile obtained of formula (I),

is reacted in the presence of a solvent with sodium azide to give a corresponding fluoroalkyltetrazole of formula (III)

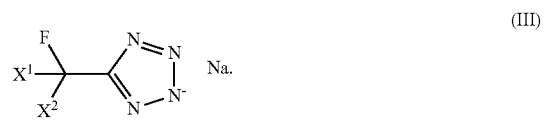

10. The process according to claim 9, wherein the fluoroalkylnitrile of formula (I) is obtained and, after cooling and scrubbing, is led to a mixture of solvent and sodium azide.

* * * * *